(12) United States Patent
Hayward et al.

(10) Patent No.: US 9,253,977 B2
(45) Date of Patent: Feb. 9, 2016

(54) ENCAPSULATED WOOD PRESERVATIVES

(71) Applicant: Tapuae Partnership, New Plymouth (NZ)

(72) Inventors: Peter James Hayward, New Plymouth (NZ); Wallace James Rae, New Plymouth (NZ); Jarrett Malcolm Black, New Plymouth (NZ)

(73) Assignee: Tapuae Partnership, New Plymouth (NZ)

( * ) Notice: Subject to any disclaimer, the term of this patent is extended or adjusted under 35 U.S.C. 154(b) by 108 days.

(21) Appl. No.: 13/769,995

(22) Filed: Feb. 19, 2013

(65) Prior Publication Data

US 2014/0057095 A1    Feb. 27, 2014

Related U.S. Application Data

(63) Continuation of application No. 12/918,953, filed as application No. PCT/NZ2008/000022 on Feb. 22, 2008.

(51) Int. Cl.
| | | |
|---|---|---|
| *A01N 25/28* | (2006.01) | |
| *B32B 21/04* | (2006.01) | |
| *A01P 3/00* | (2006.01) | |
| *B27K 3/00* | (2006.01) | |
| *A01N 53/00* | (2006.01) | |
| *B27K 3/34* | (2006.01) | |

(52) U.S. Cl.
CPC ............... *A01N 25/28* (2013.01); *A01N 53/00* (2013.01); *B27K 3/005* (2013.01); *B27K 3/34* (2013.01); *Y10T 428/249921* (2015.04); *Y10T 428/25* (2015.01); *Y10T 428/254* (2015.01)

(58) Field of Classification Search
CPC ....... A01N 25/04; A01N 25/12; A01N 25/28; A01N 33/12; A61K 2800/412; A61K 2800/413; A61K 9/5192; B27K 3/007; B27K 3/08; B27K 3/15; B27K 3/34; B27K 3/16; C09D 5/14; C08K 5/0058; C08K 3/005

USPC ......... 428/402–402.24, 403, 404, 407, 321.1, 428/474.4; 427/331, 389.9, 212, 427/213–213.36, 483, 256; 264/34, 5, 41, 264/4–4.7; 424/463, 452, 400, 408, 450, 424/451, 455, 93.7, 184.1, 497, 489, 501, 424/490, 491, 492, 493, 494, 495; 106/287.26
See application file for complete search history.

(56) References Cited

U.S. PATENT DOCUMENTS

| | | | | |
|---|---|---|---|---|
| 5,837,290 | A | * | 11/1998 | Hasslin .......................... 424/489 |
| 2002/0051892 | A1 | * | 5/2002 | Laks et al. .................... 428/541 |
| 2004/0258767 | A1 | | 12/2004 | Leach et al. |
| 2005/0221991 | A1 | | 10/2005 | Wolf et al. |
| 2006/0003897 | A1 | | 1/2006 | Bell |
| 2007/0036832 | A1 | | 2/2007 | Williams et al. |

FOREIGN PATENT DOCUMENTS

| | | |
|---|---|---|
| JP | 59025308 | 2/1984 |
| JP | 02022201 | 1/1990 |
| JP | 09110621 | 4/1997 |
| WO | 2006091113 | 8/2006 |
| WO | 2007039055 | 4/2007 |
| WO | 2007070769 | 6/2007 |

OTHER PUBLICATIONS

Written Opinion for PCT Application PCT/NZ2008/000022 and International Search Report for PCT Application PCT/NZ2008/000022.

* cited by examiner

*Primary Examiner* — James J Seidleck
*Assistant Examiner* — S. Camilla Pourbohloul
(74) *Attorney, Agent, or Firm* — Garcia-Zamor IP Law; Ruy M. Garcia-Zamor

(57) ABSTRACT

A method of incorporating biocides into wood or a wood product, the method including the steps of synthesizing a plurality of capsules each having an outer shell of polymer and incorporating within each said capsule an additive which includes an organic biocide, and then applying the said capsules to the wood or wood product in a manner whereby the capsules penetrate the wood or wood product.

8 Claims, 2 Drawing Sheets

Analysis of blocks:

a: inner 9th b: Outer middle 9th

Table 2

| Formulation & mean p.s. | Estimated Average retention g/m$^3$ | Inner 9$^{th}$ core retention g/m$^3$ | Outer middle 9$^{th}$ retention g/m$^3$ |
|---|---|---|---|
| Bifenthrin encaps. 3.3μ | 95 | 111 | 85.4 |
| Bifenthrin encaps. 5μ | 105 | 115 | 74.1 |
| Bifenthrin encaps. 9.2μ | 103 | 77.2 | 78.3 |
| Bifenthrin encaps. 20 μ | 106 | 8.8 | 27.4 |
| Bifenthrin encaps. 9.2μ | 103 | 77.2 | 78.3 |
| Bifenthrin SC 9.2μ | 108 | 18 | 133 |

Figure 2

ENCAPSULATED WOOD PRESERVATIVES

FIELD OF THE INVENTION

The present invention relates to encapsulated wood preservatives for wood treatment.

BACKGROUND

As a biological material, wood is subject to attack by fungi and insects. These organisms may damage the appearance of the wood, and they may seriously reduce its structural strength. Wood and wood based products can be protected from wood destroying organisms by applying fungicides or insecticides, or both. Such treatments can greatly improve the service life of the wood product, especially for timbers with low natural durability, such as radiata pine.

In recent times there has been increased scrutiny of the emission of preservatives, not only during the treatment process, but from the wood after treatment.

For instance concern has been expressed with regard to the toxicity of residual arsenic in Copper Chrome Arsenic (CCA) treated wood. CCA has a long history as a low cost and effective wood preservative, but is now being excluded from certain applications where human exposure to the wood in service is high, such as playground equipment and decking. Inorganic preservatives also face the disadvantage of residual toxicity from waste. Incineration of wood waste creates volatile emissions of the heavy metals. The remaining ash will also contain toxic metal residues. Heavy metals from wood waste such as sawdust and offcuts persist in landfill and potentially pose a risk of contaminating water supplies.

Alternative, environmentally more benign, organic preservatives still have issues with regard to their application as wood preservatives.

CCA has a proven history of preserving wood over a broad range of environments, with an expectation of a service life of 25 to more than 50 years. Organic preservatives, being based on carbon chemistry, have a less certain durability. Service life must be extrapolated from field experiments typically lasting from five to ten years.

Over a time frame of 25 years or more there are additional mechanisms which might diminish the effectiveness of organic preservatives.

For instance, azoles have a limited number cell activity sites which could eventually lead to resistance and therefore might be better combined with other biocides such as the heavy metal copper. Also since they have weak bacterial activity they could eventually be subject to bacterial biodeterioration. Whereas broader spectrum biocides, such as 2-(thiocyanomethylthio)benzothiazole (TCMTB) and 4,5-dichloro-2-n-octyl-4-isothiazolin-3-one (Kathon 925), which have found utility as in wood treatments, are skin irritants.

Similarly Lambda-cyhalothrin cypermethrin, deltamethrin, and bifenthrin all have a degree of paraesthesia and toxicity which makes them difficult to use in wood treatment processes.

Chlorpyrifos has appreciable vapour pressure and malodour at ambient temperatures—losses will occur through evaporation.

Iodocarb, a broad spectrum biocide, hydrolyses in the presence of light and moisture over months rather than years.

A further issue with many of the organic biocides currently in use is that while they are sparingly water soluble, even this limited solubility is sometimes insufficient to resist leaching over a protracted period.

While light organic solvent carriers can be used to allow impregnation of the wood with preservative, they are undesirable as they increase expense and raise other issues of volatile organic hydrocarbon emissions into the environment. Similarly, solubilisation with surfactants to form an aqueous micro-emulsion of the active allows the use of lower cost water as a carrier, but increases the propensity of the active to leach.

Conventional methods of applying preservative treatment require a pressure difference to create an influx of fluid into the wood structure. Freshly felled wet wood freely conducts aqueous solutions. Preservative solutions may hydraulically displace the sap. More reliable treatments are achieved by first drying the timber and at least temporarily filling the empty wood cells with preservative solution. During initial drying, modification of the wood structure occurs reducing the ability of aqueous solutions to penetrate.

The most important modification from a treatment perspective is the aspiration of compound pits where the suspended torus seals up the pit opening leading to a reduction in permeability. However certain soft wood species, notably pinus radiata, can be satisfactorily treated after drying. Aqueous solutions of preservatives are pumped into the dry wood at pressures of up to 1400 Kpa which is sufficient to reopen the interconnections between the wood cells.

Pit size of softwood species is highly variable. Tracheids, one of the main types of softwood wood cell, vary in size up to a few millimeters in length, and are in diameter about 60 μm.

In green timber pit diameters vary from between 2 μm to 10 μm depending on the size of the tracheid. It is assumed that the torus in the centre of the pit which collapses across the pit opening during drying is dislodged during pressure treatment. To satisfactorily penetrate "treatable" softwood timbers it has been assumed that particulate actives must have diameters substantially less than 10 μm.

It is an object of the present invention to overcome one or more of the various disadvantages of the prior art as discussed, or at least to provide the public with a useful choice.

SUMMARY OF THE INVENTION

In a first broad embodiment the present invention provides a method of incorporating biocides into wood or a wood product, the method including the steps of synthesising a plurality of capsules each having an outer shell of polymer and incorporating within each said capsule an additive which includes an organic biocide, and then applying the said capsules to the wood or wood product in a manner whereby the capsules penetrate the wood or wood product.

The term "organic biocide" unless specifically stated otherwise, is intended to refer to fungicides, insecticides, mouldicides, bactericides, algaecides or any other compound which serves as a protectant agent for wood preservation.

An advantage of the organic biocide being in the form of an encapsulated active is that it is less likely, in use, to give rise to toxicity or sensitivity in handlers of the preservative and which can effectively penetrate wood.

Preferably the organic biocide comprises at least one of an insecticide or a fungicide.

Desirably the organic biocide comprises at least one of an isothiazolone a pyrethroid, a neonicotenoid, a halogenated carbamate, an azole or a combination thereof.

More preferably the biocide comprises at least one of, 4,5-dichloro-2-nOctyl-4-lsothiazolin-3-one (DCOIT), chlorothalonil, bifenthrin and combination thereof.

Preferably the capsules are applied to the surface of the wood or wood product in the form of a suspension by spraying, dipping or soaking.

More preferably the method further involves applying sufficient pressure is the suspension of capsules to force the capsules to penetrate into the to wood or wood product.

A further advantage of employing the method of the present invention is that the preservative is retained in the wood in an effective amount for a greater period of time with a minimum amount of active being dissipated or degraded in the environment.

A still further advantage of the present invention is that encapsulated organic biocides show a degree of penetration into solid wood at particle sizes up to 20 microns and are clearly superior in penetration to the same active in a micronised state of a similar particle size.

Preferably 95% of the capsules are less than 20.

The utility of this invention is of particular advantage to those preservatives that are otherwise limited in their end use because of their volatility, leachability, toxicity, skin irritancy or solvency.

The present invention allows micro-emulsions of organic biocides to be used to impregnate wood products with a significant reduction in organic solvents. The high surfactant loadings used to solubilise the organic phase also reduces the fixing of the organic actives during leaching.

Desirably the invention has application to wood or wood products formed from at least one of solid wood, orientated strand board, particle board, medium density fibrewood, plywood, laminated veneer lumber, laminated strand lumber, and hardboard.

Optionally the organic biocide is one or more of azoles, isothiazolinones, carbamates, benzothiazoles, chloronitriles, pyrethroids etc. or mixtures thereof.

Preferably the organic biocides exhibit high solubility in a water immiscible solvent. The encapsulated organic biocide can be made by dissolving the active in a water immiscible solvent containing a reactive oil soluble prepolymer. Emulsifying the oil in an aqueous phase containing a reactive polymerisation initiator creates a capsule wall at the oil water interface.

The encapsulated organic biocides can optionally be mixed with other water soluble biocides such as quaternary ammonium compounds metal or boron salts, or other penetrating adjuvants such as fatty amine oxides.

In one preferred embodiment the encapsulated preservative may be applied by diluting in a fluid prior to application by pressure. The sizes of the encapsulated particles of organic biocide are preferably between 0.1 and 20 microns.

Standard vacuum and or pressure methods may be used to impregnate the wood. The standard processes are defined as described in New Zealand Timber Authority Specifications 1986, P2 Rueping (Empty Cell Process), P4 the Bethell Process, P5 the Lowry Process, and P9 the Alternating Pressure Method.

DESCRIPTION OF THE DRAWINGS

FIG. 2 is the degree of penetration of encapsulated bifenthrin.

DESCRIPTION OF A PREFERRED EMBODIMENT

Three samples of pines radiata 10%-15% moisture content; dimensions 40×90×500 mm were cut weighed and end sealed. A formulation of either an encapsulated product or a suspension concentrate was diluted to achieve an estimated final retention of 100 g/m3 by the Bethell P4 full cell process.

Figure 1:
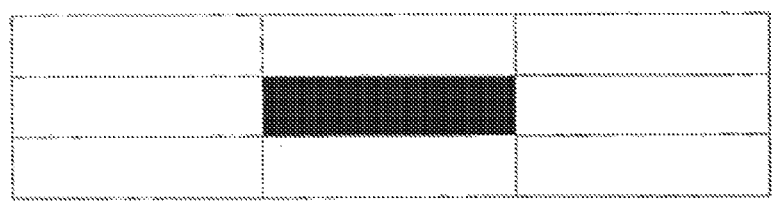
FIG. 1 is the assayed bifenthrin in the inner ninth core and the outer middle 9th segment.
Figure 1:
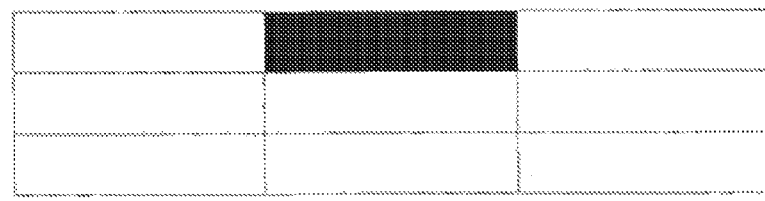

After each treatment the gross fluid retentions were measured by weighing and the average active content estimated by calculation. Samples were fillet stacked and allowed to air dry for three weeks. The inner ninth core samples were then ground, extracted and analysed by g.c. for actual bifenthrin assay (shown in FIG. 1).

The assayed bifenthrin in the inner ninth core, the outer middle 9th segment was then compared to the estimated average retention to compare the degree of screening of the various formulations.

FIG. 2 shows that the degree of penetration of encapsulated bifenthrin gives full penetration up to a mean capsule size of about 9 microns, whereas the micronised bifenthrin is screened out at the same mean particle size. Capsules of 20µ mean capsule size were severely screened.

While the present invention has been illustrated by the description of an embodiment thereof, and while the embodiment has been described in detail, it is not the intention of the applicants to restrict or in any way limit the scope of the appended claims to such detail.

Additional advantages and modifications will readily appear to those skilled in the art. Therefore, the invention in its broader aspects is not limited to the specific details, representative methods, and illustrative example shown and described.

Accordingly, departures may be made from such details without departure from the spirit or scope of the Applicant's general inventive concept as detailed in the appended claims.

What we claim is:

1. A microencapsulated organic biocidal composition for impregnating a wood or timber product comprising a plurality of microcapsules each comprising a water immiscible solvent surrounded by a polymeric outer shell, the water immiscible solvent containing one or more organic biocides selected from fungicides, insecticides, and a combination thereof, wherein the one or more insecticide or fungicide is selected from the group consisting of an isothiazolone, a benzothiazole, a pyrethroid, a neonicotinoid, a halogenated carbamate, an azole, a chloronitrile, or a combination thereof, and further characterized in that the mean microcapsule diameter is between about 1.5 microns and about 20 microns such that impregnation of a wood or timber product results in retention of a biocidally effective amount of said biocides within the inner ninth core of said product, wherein the composition is diluted in water.

2. The composition according to claim 1 wherein the composition is and applied to the wood or timber product using standard industry vacuum and or pressure treatment methods to force the microcapsules to penetrate into the inner ninth core and resulting in a biocide retention within the inner ninth core exceeding 75% of the estimated average biocide retention.

3. The composition according to claim 1 wherein the mean microcapsule diameter is less than about 9.2 microns.

4. The composition according to claim 1 wherein the one or more insecticide or fungicide is selected from the group consisting of 4,5-dichloro-2-n-octyle-4-isothiazoline-3-one (DCOIT), chlorothalonil, bifenthrin, and a combination thereof.

5. The composition according to claim 1 wherein the microencapsulated organic biocide further comprises one or more additional water soluble biocides and/or other penetrating adjuvants.

6. The composition according to claim 5 wherein the additional water soluble biocides are quaternary ammonium compounds, metal salts or boron salts.

7. The composition according claim 1 wherein the wood or timber product is at least one of solid wood, orientated strand board, particle board, medium density fibrewood, plywood, laminated veneer lumber, and laminated strand lumber.

8. A wood or timber product impregnated with the microencapsulated organic biocidal composition of claim 1.

* * * * *